US008061350B2

(12) United States Patent
Boeck et al.

(10) Patent No.: US 8,061,350 B2
(45) Date of Patent: Nov. 22, 2011

(54) PROCESS AND DEVICE FOR DOSING PHARMACEUTICAL AGENTS

(75) Inventors: Georg Boeck, Laupheim (DE); Johannes Geser, Ingelheim (DE); Matthias Hausmann, Dortmund (DE); Hans-Juergen Koelbel, Siegburg (DE); Joachim Eicher, Dortmund (DE); Christian Feiertag, Sprockhoevel (DE)

(73) Assignee: Boehringer Ingelheim Pharma GmbH & Co. KG, Ingelheim (DE)

(*) Notice: Subject to any disclaimer, the term of this patent is extended or adjusted under 35 U.S.C. 154(b) by 1450 days.

(21) Appl. No.: 11/421,928

(22) Filed: Jun. 2, 2006

(65) Prior Publication Data

US 2007/0282276 A1 Dec. 6, 2007

(51) Int. Cl.
*A61M 16/00* (2006.01)

(52) U.S. Cl. ......... 128/200.14; 128/200.21; 128/203.23; 128/203.12; 128/203.24; 128/205.18; 128/205.24; 128/200.24; 128/200.22

(58) Field of Classification Search ............ 128/200.14, 128/200.21, 200.23, 200.24, 203.12, 203.23, 128/203.24, 205.18, 205.24
See application file for complete search history.

(56) References Cited

U.S. PATENT DOCUMENTS

| | | | | |
|---|---|---|---|---|
| 5,497,944 | A | 3/1996 | Weston et al. | |
| 5,511,538 | A * | 4/1996 | Haber et al. | 128/200.14 |
| 5,964,416 | A | 10/1999 | Jaeger et al. | |
| 6,176,492 | B1 | 1/2001 | Sawai | |
| 6,916,159 | B2 * | 7/2005 | Rush et al. | 417/321 |
| 2004/0134495 | A1 * | 7/2004 | Eigemann et al. | 128/203.15 |
| 2005/0247305 | A1 | 11/2005 | Zierenberg et al. | |
| 2007/0087309 | A1 * | 4/2007 | Campion | 433/141 |

FOREIGN PATENT DOCUMENTS

| | | | |
|---|---|---|---|
| DE | 1058440 | | 5/1959 |
| DE | 1750809 | | 12/1971 |
| DE | 10361 735 | A1 | 7/2005 |
| EP | 1 003 478 | B1 | 8/2005 |
| WO | WO 99/65464 | A1 | 12/1999 |
| WO | 2005/080001 | A1 | 9/2005 |
| WO | WO 2007051536 | A1 * | 5/2007 |

OTHER PUBLICATIONS

Matching Problems in Selective Assembly Operations, C.R. Coullard, A.B. Gamble and P.C. Jones, Annals of Operations Research 76(1998)95-107.

* cited by examiner

*Primary Examiner* — Justine Yu
*Assistant Examiner* — Clinton Ostrup
(74) *Attorney, Agent, or Firm* — Roberts Mlotkowski Safran & Cole, P.C.; David S. Safran

(57) ABSTRACT

A process and a device for dosing a pharmaceutical agent, preferably a liquid, are proposed. To achieve an enhanced dosing accuracy, a first component that is produced in batches, such as a shaped seal, is combined with a second component, such as a guide pipe selected from a suitable group guide pipes, wherein the suitable group of second components is selected based on at least one decisively significant value of the respective batch first components and is distinguished by an essential value of the second component which will optimize the sealing between the first and second components.

10 Claims, 1 Drawing Sheet

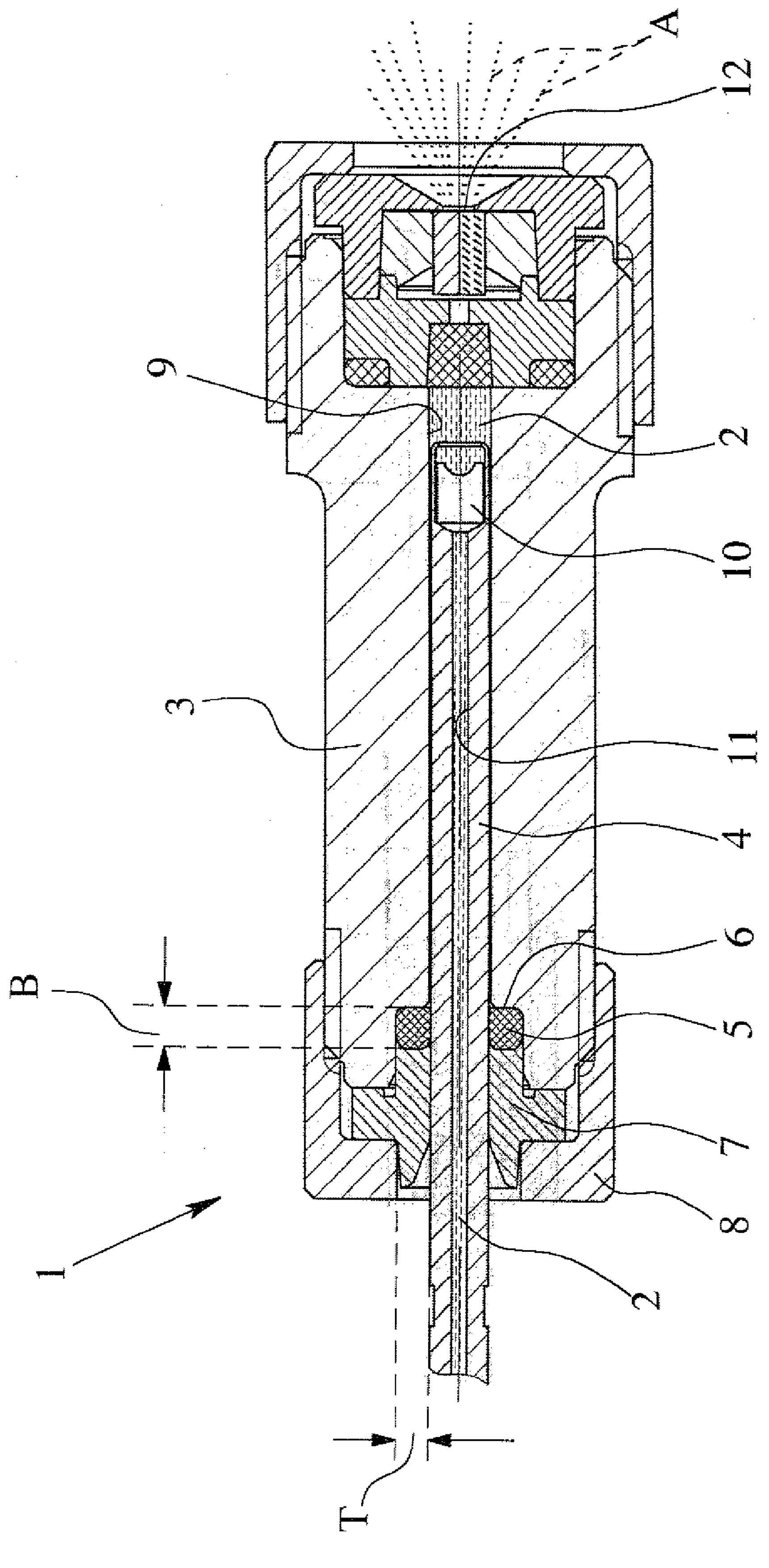
A
12
9
2
10
3
11
4
6
B
5
7
8
1
2
T

PROCESS AND DEVICE FOR DOSING PHARMACEUTICAL AGENTS

BACKGROUND OF THE INVENTION

1. Field of Invention

This invention relates to a process for producing a pharmaceutical agent, in particular as an aerosol, with enhanced dosing accuracy, as well as a device for administering a pharmaceutical agent, in particular as an aerosol, with enhanced dosing accuracy.

2. Description of Related Art

In this invention, the term "pharmaceutical agent" is defined, in particular, as pharmaceutical agent formulations or pharmaceutical agent mixtures. The pharmaceutical agent is preferably present in liquid form, wherein it may be a suspension, a solution or a mixture of the two (a so-called suslution). In addition, it can be a powder. The following description of the invention focuses primarily on a pharmaceutical agent in liquid form, so that often only liquid is spoken of, but this correspondingly applies for other pharmaceutical agents, and for comparable substances, in terms of this invention.

European Patent Application EP 1 426 662 A1 and corresponding U.S. Patent Application Publication 2004/0134495, which forms the starting point of this invention, discloses a device for dosing or dispensing a liquid, in particular, a pharmaceutical liquid. The known device has a guide pipe with a piston that travels therein as well as an O-ring seal to ensure sealing between the guide pipe and piston. The O-ring seal is arranged in a groove of the guide pipe. To achieve a good seal, a groove fill level of more than 90% through the O-ring seal is provided. In practice, it has been shown that the tolerances of the individual components can lead to an inadequate seal, in particular against air, and thus, to an inadequate dosing accuracy. An exact dosage is essential, however, specifically in the administration of pharmaceutical agents or the like, to which this invention relates.

SUMMARY OF THE INVENTION

A primary object of this invention is to indicate a process and a device with enhanced dosing accuracy for producing or administering pharmaceutical agents, in particular as aerosols.

The above-mentioned object is achieved according to the invention, in terms of the process, by a first and a second component being used, wherein the first component is produced in batches, wherein at least one significant value of the first components of any batch is determined on a random-sample basis and at least one decisively significant value is determined for all first components of the respective batch, wherein the second component is divided into groups that are distinguished by at least one essential value of the second components, wherein based on at least one decisively significant value, a suitable group is selected, wherein a first component of a batch is preferably combined or incorporated exclusively with a second component of a group suitable to this batch. By selecting a corresponding, suitable group of two components, an enhanced sealing between the combined components, which preferably are moved relative to one another to produce the pharmaceutical agent, is made possible. Thus, an enhanced dosing accuracy is achieved.

The process is suitable, in particular, for very small components that are produced, for example, with a microstructure or have dimensions of only a few 10 μm to about 3 mm, preferably for diagnostic pharmacy. For example, the first components are injection-molded and preferably form ring-shaped seals, in particular O-rings.

As significant values of the first components, in particular in ring-shaped seals, such as O-rings, preferably the volume and/or the compressibility are determined.

It has been shown that it is sufficient to detect or to determine the mean and the standard deviation, for example, the volume and the compressibility, as significant values of the first components. This allows for a comparatively small expense.

The second components preferably have a recess, in particular a shoulder or a groove, for incorporation of the first component, and they form in particular a guide pipe for a piston of the device. As a value that is significant for division of the second components into groups, preferably a value that relates to the recess, such as the depth and/or width of the recess, is used. It has been shown that these values or dimensions are adequate for the division, such that only a comparatively lesser expense is necessary.

In turn, preferably the mean and the standard deviation, in particular, the depth and/or width of the recess, are used as values that are significant for division into groups.

The second components are preferably produced specifically with different essential values, wherein the values can differ by more than the production tolerance to produce and prepare different groups of the second components. The production with different essential values is carried out preferably based on need or on statistical probability.

The second components are preferably also produced in batches but, in particular, with different essential values wherein the essential value of the second component is determined on a random-sample basis from each batch and the essential value for all second components of the respective batch is determined therefrom. Thus, an individual measurement of the second components can be avoided and thus the expense as a whole can be kept low.

The above-mentioned object is achieved, according to the invention, in terms of the device, via the first and second components especially preferably having at least one additional component, in particular several additional components, such as a piston, which is sealed by the first component, and a support ring for axial securing of the component on the second component. If any batches of the first and additional components are now combined, a desired setpoint can be reached by selection of a suitable group of the second component that is thus "variable" at least in its essential value. For this variation, in particular, the depth dimension of the recess, thus the guide pipe, and/or the width (axial length) of the recess, thus, for example, a support ring for immobilizing a seal as a first component in the recess, is suitable.

To be able to select the suitable group when the device with the first and second components has at least one additional component, one or more additional significant value(s) of the additional component or the additional components, in particular the diameter of the piston and/or the axially effective length of the support ring, is or are determined and is or are taken into consideration as (an) additional significant value(s) in addition to the decisively significant values in the selection of the suitable group.

As already explained, the suitable group is selected such that the decisively significant value together with optionally other significant values and the essential value in the manufactured device—at least on average—results in a specific setpoint, in particular a set fill level of the recess of a shaped seal. The selection is made, in particular, with computer support with consideration of error propagation and/or statistical methods.

Relative to this invention, the term "fill level" is defined, in particular, as the quotient of the volume of the incorporated seal divided by the volume of the recess.

In this invention, the term "shaped seal" is defined as both flat gasket rings and O-ring seals as well as other shaped seals, i.e., with deviating cross-sectional shapes. The shaped seals are preferably designed as through-going rings.

Above, the process according to the proposal was explained in general but with reference to the preferred application in a device for dispensing or dosing of a liquid, and preferably, of a pharmaceutical agent. The process according to the proposal can generally be used in any type of device. The preferred application is with devices that are built from microcomponents whose individual measurement would produce a considerable expense. Below, emphasis is primarily placed on a device according to the proposal.

A device according to the invention for administration of a pharmaceutical agent, in particular, for dispensing or dosing a liquid, has a guide pipe with a long-travel piston, a shaped seal to ensure sealing between guide pipe and piston, as well as a recess for receiving the shaped seal, wherein the shaped seal of a specific batch of shaped seals is combined with a guide pipe of a suitable, specific group, wherein the group is selected from several groups of guide pipes based on at least one decisively significant value of the batch to fill up the recess through the shaped seal with a set fill level. Thus, in a comparatively simple way, a specific set fill level, which ensures the desired seal, and thus, an enhanced dosing accuracy can be achieved.

In the selection of the suitable group, tolerances or values of additional components, in particular significant values of batches of other components, such as diameter of the piston, effective axial length of the support ring for axial support of the shaped seal or limitation of the groove or the like, can also be considered.

Other aspects, properties, advantages and features of this invention will become apparent form the following detailed description of a preferred embodiment in accordance with the accompanying drawing.

BRIEF DESCRIPTION OF THE DRAWINGS

The sole FIGURE is a diagrammatic cross-sectional view of a device according to the proposal.

DETAILED DESCRIPTION OF THE PREFERRED EMBODIMENTS

The device 1 according to the illustrated embodiment of the invention for administering or dispensing, in particular, for dispensing or dosing, a pharmaceutical agent, preferably a liquid 2, is designed, in particular, for very small pump volumes or dosages. In the illustrative example, the pump volumes are 1 μl to 1 ml, preferably 1 μl to 500 μl, in particular 5 μl to 100 μl, quite especially preferably 5 μl to 30 μl, and in particular, essentially 15 μl, per piston stroke.

To be able to ensure delivery of a specific desired volume, in particular, even in the case of a first actuation after extended non-use, no air should enter into device 1, since otherwise the dosage is no longer in the desired accuracy.

Device 1 has a guide pipe 3 (second component), a long-travel piston 4 (additional component) and a shaped seal 5 (first component) in a recess 6 as well as optionally a support ring 7 (additional component) for securing seal 5.

Guide pipe 3, optionally together with support ring 7, forms recess 5, which surrounds the piston 4 in an annular manner and in particular is designed as a groove, here as a ring groove. In the illustrative example, support ring 4 forms an axial side or limiting of recess 5, so that guide pipe 3 essentially forms a ring shoulder and a radial outside constraint for recess 5.

If necessary, recess 5 can also be designed separately from guide pipe 3.

In the illustrative example, piston 4 has a circular cross section with a diameter of 0.25 mm to 4 mm, preferably 0.5 mm to 3 mm, in particular 0.75 mm to 2.25 mm.

Piston 4 preferably is made of metal, in particular high-grade steel. It is designed, in particular, as a hollow pipe or capillary. Piston 4 is preferably drawn and consequently has a relatively low tolerance with respect to its diameter.

Shaped seal 5 is preferably designed in a through-going annular manner corresponding to recess 6. In particular, shaped seal 5 is an O-ring with an at least essentially circular cross-section in the uninstalled state.

In the illustrative example, the cross-section or the cord thickness of uninstalled shaped seal 5 is 0.3 mm to 3 mm, preferably 0.5 mm to 2 mm, in particular 1 mm to 1.5 mm. The inside diameter corresponds approximately to the piston diameter.

Shaped seal 5 preferably made of silicone or another rubber-elastic material that is suitable, in particular, for pharmaceutical agents or food.

In the installed state—i.e., in the assembled device 1—seal 5 is taken up at least essentially in recess 6. Support ring 7 axially adjoins and axially fixes the shaped seal 5 in recess 6. In addition, shaped seal 5 radially adjoins piston 4 which penetrates the shaped seal 5 in a sealing manner. Shaped seal 5 is pressed or deformed in recess 6. Shaped seal 5 has an essentially rectangular shape in cross-section, deviating from its uninstalled configuration, in cross-section or at least at a flat side contiguous with piston 4.

The "fill level" corresponds to the quotient from the volume of the incorporated shaped seal 5 through the volume of recess 6. To be able to achieve a good seal and consequently accurate dosing of device 1, the desired fill level, thus the "set fill level" in the agent is preferably 90%, in particular less than 95%, with a tolerance of at most 5%, in particular 4% or less.

In the illustrative example, support ring 7 is preferably attached by a cap-shaped holding element 8 or the like to guide pipe 3. By corresponding axial or frontal attachments, a defined length of support ring 7 and thus a defined width B (axial length) of recess 6 for shaped seal 5 is achieved.

In addition, the volume of recess 6 is decisively determined by depth T of recess 6 in guide pipe 3, i.e., the radial extension of recess 6.

Piston 4 borders a pump chamber 9 in guide pipe 3. Piston 4 is preferably provided with a nonreturn valve 10, which is located, in particular, on the end of piston 4 that faces pump chamber 9.

In the illustrative example, the preferably hollow piston 4 forms a supply channel 11 for liquid 2. With the corresponding axial movement, liquid 2 can be delivered, in particular, by aspiration, through supply channel 11 via the intake valve or the nonreturn valve 10 into pump chamber 9.

On the pressure or output side, device 1 optionally has an exhaust valve (not shown), and, for example, a nozzle 12 for exhaust and optionally spraying of liquid 2.

Shaped seals 5 are produced in batches—thus in groups. In particular, a batch that consists of a specific amount of starting materials that are as homogeneous as possible is produced.

Shaped seals 5 are preferably produced by injection-molding, in particular, by means of an injection-molding tool (not shown) with a plurality of cavities. Accordingly, in each injection-molding process, a plurality of shaped seals 5 is produced.

Shaped seals 5 can vary from batch to batch, in particular, with respect to significant sizes, such as ring diameter, cross-section, volume, compressibility or the like. In addition to dimensions (ring diameter, thickness, and/or volume) that are imposed by the tools, values that are material-related or values that are produced by process technology, such as compressibility, can also vary.

Shaped seals 5 represent first components in terms of the process according to the proposal. The significant values (in particular, only volume and compressibility) of shaped seals 5 are preferably determined only for a portion of all shaped seals 5 of a batch, and decisively significant values, in particular, mean value and standard deviation, taking into consideration the varied influences of dimensions and tolerances imposed by the tools as well as optionally other dimensions, and keeping in mind the distribution function, are determined therefrom.

According to the proposal, guide pipe 3 is classified preferably based only on an essential value in the illustrative example based on depth T of recess 6. Guide pipes 3 represent second components in terms of the process according to the proposal, and thus, are divided into different groups based on depth T. In particular, guide pipes 3 are produced with different depths T to be able to prepare the necessary groups of guide pipes 3. The groups in depth T, in each case, are preferably distinguished from one another by more than the production tolerance.

According to the proposal, a first component, i.e., a shaped seal 5, of a specific batch is combined or assembled only with a second component, i.e., a guide pipe 3, of a group that is suitable to the specific batch. The group that is suitable to the respective batch is selected based on at least one decisively significant value of this batch, in particular, based on the mean and standard deviation of the volume and compressibility of shaped seals 5 of this charge, in such a way that the essential value, i.e., in particular depth T of recess 6, of the respective groups results in a desired setpoint, here, the set fill level, or a specific seal in device 1. The selection is made in particular with consideration of error propagation and available groups.

In the illustrative example, device 1 has additional components, namely piston 4 and support ring 7, whose sizes or dimensions for reaching the setpoint, i.e., the set fill level; of respective device 1 are decisive. Consequently, preferably also the significant values of the additional components, in particular, the diameter of piston 4 and width B of recess 6, stated more specifically, the values of support ring 7 and guide pipe 3 that are decisive in this respect, are determined preferably on a random-sample basis, and additional significant values, in particular, mean value and standard deviation, are determined therefrom. These additional significant values are preferably taken into consideration in addition in the above-mentioned selection of the group of guide pipes 3 to reach the desired setpoint, i.e., set fill level, and thus, the desired sealing and dosing accuracy.

The indicated values, such as volume, compressibility, depth, width or the like, should represent values that are possibly significant only by way of example. Depending on the design and structure of device 1, production of the component, and in particular, tolerances of the components, additional and/or other values can be used as significant and/or essential values. As an alternative or in addition, other values can also be used as setpoints instead of the fill level. Instead of guide pipe 3, other components can serve as "variable" components—i.e., components divided into groups with different essential values—can also be combined with batches of other components for achieving a setpoint or an improved dosing accuracy in finished device 1.

To dose liquid 2 or the pharmaceutical agent, the first and second components, thus in particular guide pipe 3 and shaped seal 5, are moved relative to one another, wherein the combination of the components according to the proposal leads to an optimal sealing between the components and thus an improved dosing accuracy in the production or in the administration.

In the illustrative example, device 1 according to the proposal is designed in particular, as a sprayer or an inhaler. Liquid 2 is drawn off by piston 4 with a corresponding axial back-and-forth motion alternately through supply channel 11 into pump chamber 9 or is pressurized there and dispensed via nozzle 12, and in this case, dispensed or administered, preferably sprayed; thus, a spray mist or aerosol A is formed from liquid 2, as indicated in the FIGURE.

Device 1 is especially preferably designed as a sprayer or inhaler, as in the basic principle in International Patent Application Publication No. WO 91/14468 A1 and corresponding U.S. Pat. No. 5,497,944 and in a concrete embodiment in International Patent Application Publication No. WO 97/12687 A1 (FIGS. 6a, 6b) and corresponding Canadian Patent Application 2 473 681, as well as in FIGS. 1 and 2 of International Patent Application Publication No. WO 2005/080001A1 and corresponding U.S. Patent Application Publication 2005/0247305. Quite preferably, this is the sprayer or inhaler that is offered under the trademark RESPIMAT® by Boehringer Ingelheim GmbH.

However, device 1 can also be used, for example, as a metering pump, in particular, for accurate supply of pharmaceutical agents or the like, in particular as explained in the above-mentioned European Patent Application EP 1 426 662 A1 and corresponding U.S. Patent Application Publication 2004/0134495.

In particular, device 1 is a medical device. Liquid 2 is preferably a pharmaceutical agent, as already explained initially, or a medication, therapeutic agent, diagnostic agent or the like.

Device 1 can also be used, in particular, to make provide one or several active ingredients or pharmaceutical agents; if several active ingredients or pharmaceutical agents are to be dispensed, they are preferably provided at the same time. In this case, liquid 2 is, in particular, a solution. The principle of the suslution is based on the fact that several active ingredients in a formulation can be formulated together as a solution and as a suspension. In this connection, reference is made to European Patent Application EP 1 087 750 A1.

Device 1, however, can also be used in principle for cosmetic purposes or for other purposes.

Below, preferred components and/or formulations of the pharmaceutical agent or liquid 2 are cited:

As pharmaceutically active substances, substance formulations or substance mixtures, all compounds that can be inhaled are used, such as, e.g., macromolecules that can also be inhaled, as disclosed in European Patent Application EP 1 003 478 A1. Substances, substance formulations or substance mixtures for treating diseases of the respiratory system that are used in the inhalational area preferably are used.

Especially preferred in this connection are pharmaceutical agents that are selected from the group that consists of anticholinergic agents, beta-mimetic agents, steroids, phosphodiesterase IV inhibitors, LTD4 antagonists, and EGFR-kinase inhibitors, anti-allergic agents, derivatives of ergot alkaloids, 2,2,3-trimethylbutanes, CGRP antagonists, phosphodiesterase-V inhibitors, as well as combinations of such active ingredients, e.g. beta-mimetic agents plus anti-cholinergic agents or beta-mimetic agents plus anti-allergic agents. In the case of combinations, at least one of the active ingredients preferably has chemically bonded water. Anti-cholinergic agent-containing active ingredients are preferably used as monopreparations or in the form of combination preparations.

The following can be mentioned in detail as examples of the active components or their salts:

Anti-cholinergic agents that are used are preferably selected from the group that consists of tiotropium bromide, oxitropium bromide, flutropium bromide, ipratropium bromide, glycopyrronium salts, trospiumn chloride, tolterodine, 2,2-diphenylpropionic acid tropenol ester-methobromide, 2,2-diphenylpropionic acid scopine ester-methobromide, 2-fluoro-2,2-diphenylacetic acid scopine ester-methobromide, 2-fluoro-2,2-diphenylacetic acid tropenol ester-methobromide, 3,3',4,4'-tetrafluorobenzilic acid tropenol ester-methobromide, 3,3',4,4'-tetrafluorobenzilic acid scopine ester-methobromide, 4,4'-difluorobenzilic acid tropenol ester-methobromide, 4,4'-difluorobenzilic acid scopine ester-methobromide, 3,3'-difluorobenzilic acid tropenol ester-methobromide, 3,3'-difluorobenzilic acid scopine ester-methobromide, 9-hydroxy-fluorene-9-carboxylic acid tropenol ester methobromide, 9-fluoro-fluorene-9-carboxylic acid tropenol ester-methobromide, 9-hydroxy-fluorene-9-carboxylic acid scopine ester-methobromide, 9-fluoro-flurone-9-carboxylic acid scopine ester methobromide, 9-methyl-fluorene-9-carboxylic acid tropenol ester methobromide, 9-methyl-fluorene-9-carboxylic acid scopine ester methobromide, benzilic acid cyclopropyl tropine ester-methobromide, 2,2-diphenyl-propionic acid cyclopropyl tropine ester-methobromide, 9-hydroxy-xanthene-9-carboxylic acid cyclopropyl tropine ester-methobromide, 9-methyl-fluorene-9-carobyxlic acid cyclopropyl tropine ester-methobromide, 9-methyl-xanthene-9-carboxylic acid cyclopropyl tropine ester-methobromide, 9-hydroxy-fluorene-9-carboxylic acid cylopropyl tropine ester-methobromide, 4,4'-difluorobenzilic acid methyl ester cyclopropyl tropine ester-methobromide, 9-hydroxy-xanthene-9-carboxylic acid tropenol ester-methobromide, 9-hydroxy-xanthene-9-carboxylic acid scopine ester methobromide, 9-methyl-xanthene-9-carboxylic acid tropenol ester-methobromide, 9-methyl-xanthene-9-carboxylic acid scopine ester-methobromide, 9-ethyl-xanthene-9-carboxylic acid tropenol ester methobromide, 9-difluoromethyl-xanthene-9-carboxylic acid tropenol ester-methobromide, and 9-hydroxymethyl-xanthene-9-carboxylic acid scopine ester-methobromide, optionally in the form of their racemates, enantiomers or diastereomers and optionally in the form of their solvates and/or hydrates.

Beta-mimetic agents that are used are preferably selected from the group that consists of albuterol, bambuterol, bitolterol, broxaterol, carbuterol, clenbuterol, fenoterol, formoterol, hexoprenaline, ibuterol, indacaterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulfonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzenesulfonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulfonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylamino-butyl)-2H-1,4-benzoxazin-3-(4H)-one, 1-(4-amino-3-chloro-5-trifluoromethyl-phenyl)-2-tert-butylamino)ethanol and 1-(4-ethoxycarbonylamino-3-cyano-5-fluorophenyl)-2-(tert-butylamino)ethanol, optionally in the form of their racemates, enantiomers or diastereomers, and optionally, in the form of their pharmacologically compatible acid addition salts, solvates and/or hydrates.

Steroids that are used are preferably selected from the group that consists of prednisolone, prednisone, butixocort propionate, RPR-106541, flunisolide, beclomethasone, triamcinolone, budesonide, fluticasone, mometasone, ciclesonide, rofleponide, ST-126, dexamethasone, 6a,9a-difluoro-17a-[(2-furanylcarbonyl)oxy]-11b-hydroxy-16a-methyl-3-oxo-androsta-1,4-diene-17b-carbothionic acid (S-fluoromethylester, 6a,9a-difluoro-11b-hydroxy-16a-methyl-3-oxo-17a-propionyloxy-androsta-1,4-diene-17b-carbothionic acid (S)-(2-oxo-tetrahydro-furan-3S-yl)ester and etiprednol-dichloroacetate (BNP-166), optionally in the form of their racemates, enantiomers or diastereomers, and optionally, in the form of their salts and derivatives, their solvates and/or hydrates.

PDE IV inhibitors that are used are preferably selected from the group that consists of enprofylline, theophylline, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropylmethoxybenzaniide, NCS-613, pumafentine, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-[(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoro-methoxyphenyl) cyclohexan-1-one, cis[4-cyano-4(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene] acetate, (S)-(−)-ethyl[4-(3-cyclopentyl-oxy-4-methoxyphenyl)-pyrrolidin-2-ylidene]acetate, CDP840, Bay-198004, D-4418, PD-168787, T-440, T-2585, arofylline, atizoram, V-11294A, C1-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine, and 9-cyclopentyl-5,6-dihydro-7-ethyl-3-(tert-butyl)-9H-pyrazolo[3,4-c]-1,2,4-triazolo[4,3-a]pyridine, optionally in the form of their racemates, enantiomers or diastereomers, and optionally, in the form of their pharmacologically compatible acid addition salts, solvates and/or hydrates.

LTD4 antagonists that are used are preferably selected from the group that consists of montelukast, 1-(((R)-(3-(2-(6,7-difluoro-2-quinolinyl)ethenyl)phenyl)-3-(2-(2-hydroxy-2-propyl)phenyl)thio)methyl-cyclopropane-acetic acid, 1-(((1(R)-3(3-(2-(2.3 dichlorothieno[3,2-b]pyridin-5-yl)-(E)- ethenyl)phenyl)-3-(2-(1-hydroxy-1-methylethyl)phenyl) propyl)-thio)methyl)cyclopropane acetic acid, pranlukast, zafirlukast, [2-[[2-(4-tert-butyl-2-thiazolyl)-5-benzofuranyl] oxymethyl]phenyl]acetic acid, MCC-847 (ZD-3523), MN-001, MEN-91507 (LM-1507), VUF-5078, VUF-K-8707 and L-733321, optionally in the form of their racemates, enantiomers or diastereomers, optionally in the form of their pharmacologically compatible acid addition salts as well as optionally in the form of their salts and derivatives, their solvates and/or hydrates.

EGFR-Kinase inhibitors that are used are preferably selected from the group that consists of cetuximab, trastuzumab, ABX-EGF, Mab ICR-62, 4-[(3-chloro-4-fluorophenyl)amino]-6-{[4-(morpholin-4-yl)-1-oxo-2-buten-1-yl] amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluorophenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morphlin-4-yl)ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl) amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluoro-phenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethinyl-phenyl)amino]-6,7-bis-(2-methoxy-ethoxy)-quinazoline, 4-[(R)-(1-phenyl-ethyl) amino]-6-(4-hydroxy-phenyl)-7H-pyrrolo[2,3-d] pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl] amino}-7-methoxy-quinazoline, 4-[(3-chloro-4-fluoro-phenyl)amino]-6-{[4-(morpholin-4-yl)-1-oxo-2-buten-1-yl] amino}-7-[(tetrahydrofuran-2-yl)methoxy]-quinazoline, 4-[(3-ethinyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulfonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluorophenyl)amino]-6-{1-[(morpholin-4-yl) carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl) amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[piperidin-1-yl)carbonyl]-piperidin-4-yloxy}-7-methoxy-quinazoline, 4-[(3-chloro-4-fluoro-phenyl)-amino]-6-(cis-4-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethanesulfonylamino-cyclohexan-1-yloxy)-7-methoxy-quinazoline, 4-[(3-chloro-4-fluoro-phenyl)amino]-6-(1-methanesulfonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethinyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinaozline, 4-[(3-chloro-4-fluoro-phenyl)amino]-6-{cis-4-[(morpholin-4-yl) carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethinyl-phenyl)amino]-6-(1-acetyl-piperidin-4-yloxy)-7-methoxy-quinazoline, 4-[(3-ethinyl-phenyl)amino]-6-(1-methyl-piperidin-4-yloxy)-7-methoxy-quinazoline, 4-[(3-ethinyl-phenyl)amino]-6-(1-methanesulfonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-ethinyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy)-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6[cis-4-(N-methanesulfonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]6-(trans-4-methylamino-cyclohexan-1-yloxy)-7-methoxy-quinazoline, 4-[(3-chloro-4-fluoro-phenyl)amino]-6-[trans-4-(N-methanesulfonyl-N-methyl-amino)-cyclohexan-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluorophenyl)amino]-6-(1-methanesulfonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxyethyl)carbonyl]-piperidin-4-yloxy}-7-methoxy-quinazoline, optionally in the form of their racemates, enantiomers or diastereomers, optionally in the form of their pharmacologically compatible acid addition salts, their solvates and/or hydrates.

Acid addition salts with pharmacologically compatible acids that can optionally be formed by the compounds, are defined as, for example, salts that are selected from the group that consists of hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofimarate, hydrotartrate, hydrooxalate, hydrosuccinate, hydrobenzoate and hydro-p-toluene sulfonate, preferably hydrochloride, hydrobromide, hydrosulfate, hydrophosphate, hydrofimarate and hydromethanesulfonate.

As anti-allergic agents: disodium cromoglicate, nedocromil.

As derivatives of ergot alkaloids: dihydroergotamine, ergotamine.

For inhalation, pharmaceutical agents with the above-mentioned active ingredients are considered, as well as their salts, esters, as well as the combination of these active ingredients, salts and esters.

What is claimed is:

1. A process of assembling a device for delivering a medicament with improved metering accuracy, wherein at least one first component and at least one second component are provided, which are sealingly brought into engagement with one another, wherein the at least one first component is a ring-shaped seal produced in batches, wherein at least one significant magnitude of the at least one first component in each batch is selected from the diameter, cross-section, volume, or compressibility of the at least one first component and is determined only by random sampling from which the mean and the standard deviation of the at least one significant magnitude are determined, the mean and the standard deviation determined are used as essential values for division of the at least one second component into groups, wherein at least one decisive significant magnitude for all the at least one first components of the respective batch is determined from the at least one significant magnitude, wherein the at least one second component is a guide tube for a piston and is divided into groups which differ by at least one essential dimensional value of the at least one second component, wherein, depending on the at least one decisive significant magnitude, one of the groups matching the respective decisive significant magnitude, and thus, to the respective batch is selected, wherein a piston is provided which is sealed by the at least one first component, the diameter of the piston is an additional significant value, in addition to the decisively significant value, in selection of a suitable one of said groups wherein the at least one first component of a batch is combined with the at least one second component of one of the groups matching this batch and a support ring axially securing the at least one first component within the at least one second component in a deformed state so as to achieve an optimum seal between the at least one first component and the at least one second component and between the at least one first component and the piston in order to improve the metering accuracy.

2. The process according to claim 1, wherein the step of producing the at least one first component is performed by injection molding.

3. The process according to claim 1, wherein the mean and the standard deviation are determined to be significant values.

4. The process according to claim 1, wherein the at least one second component has a recess for receiving the at least one first component.

5. The process according to claim 4, wherein the recess comprises a shoulder or groove and forms the guide tube for a piston.

6. The process according to claim 1, wherein the at least one second component is produced with different essential values, and wherein the difference of the essential values of different groups is greater than production tolerances.

7. The process according to claim 1, wherein the at least one second component is produced in batches, wherein the at least one essential value of the at least one second component of each batch is determined based on a random sample, and the essential value determined from the random sample is used for all second components of the respective batch for division into groups.

8. The process according to claim 1, wherein the piston is produced in batches, and at least one significant value thereof is determined only on a random-sample basis for each batch of pistons.

9. The process according to claim 1, wherein an axially active length of the support ring is determined, and is considered as an additional significant value in addition to the decisively significant value in selection of a suitable one of said groups.

10. The process according to claim 1, wherein a suitable one of said groups is selected such that the decisively significant value together with the at least one essential value results in a set fill level of the recess by the seal.

* * * * *